US006613927B1

(12) United States Patent
Kwok

(10) Patent No.: US 6,613,927 B1
(45) Date of Patent: Sep. 2, 2003

(54) STERILE LYOPHILIZED IFOSFAMIDE AND ASSOCIATED METHODS

(75) Inventor: K. Keith Kwok, Long Grove, IL (US)

(73) Assignee: American Pharmaceutical Partners, Inc., Schaumburg, IL (US)

(*) Notice: Subject to any disclaimer, the term of this patent is extended or adjusted under 35 U.S.C. 154(b) by 82 days.

(21) Appl. No.: 10/071,598

(22) Filed: Feb. 8, 2002

(51) Int. Cl.$^7$ .................... C07F 9/02; A01N 57/04; A01N 57/12; A01N 57/28; A01N 57/36
(52) U.S. Cl. .................... 558/81; 514/90; 514/110
(58) Field of Search ................ 544/1; 558/81; 514/90, 110

(56) References Cited

U.S. PATENT DOCUMENTS

| | | |
|---|---|---|
| 3,732,340 A | 5/1973 | Arnold et al. |
| 4,537,883 A | 8/1985 | Alexander et al. |
| 4,671,331 A | 6/1987 | Pruden |
| 4,684,742 A | 8/1987 | Stec et al. |
| 4,797,388 A | 1/1989 | Francis |
| 4,879,286 A | 11/1989 | Alam et al. |
| 4,882,452 A | 11/1989 | Engel et al. |
| 4,908,464 A | 3/1990 | Stec et al. |
| 4,952,575 A | 8/1990 | Sauerbier et al. |
| 4,959,215 A | 9/1990 | Sauerbier et al. |
| 5,036,060 A | 7/1991 | Alam et al. |
| 5,066,647 A | 11/1991 | Palepu et al. |
| 5,130,305 A | 7/1992 | Palepu et al. |
| 5,204,335 A | 4/1993 | Sauerbier et al. |
| 5,227,373 A | 7/1993 | Alexander et al. |
| 5,227,374 A | 7/1993 | Alexander et al. |
| 5,268,368 A | 12/1993 | Palepu |
| 5,336,669 A | 8/1994 | Palepu et al. |
| 5,413,995 A | 5/1995 | Alexander et al. |
| 5,418,223 A | 5/1995 | Palepu et al. |
| 5,750,131 A | 5/1998 | Wichert et al. |
| 5,972,912 A | 10/1999 | Marek et al. |
| 6,136,814 A | 10/2000 | Li et al. |

FOREIGN PATENT DOCUMENTS

| | | | | |
|---|---|---|---|---|
| WO | 95/07083 | * | 3/1995 | ......... A61K/31/675 |

OTHER PUBLICATIONS

*Physicians' Desk Reference*, 56$^{th}$ Ed., Medical Economics Co., Inc., Montvale, NJ, 1123–1124 (2002).

* cited by examiner

*Primary Examiner*—Brian Davis
(74) *Attorney, Agent, or Firm*—Leydig, Voit & Mayer, Ltd.

(57) ABSTRACT

The present invention provides a stable, sterile, pharmaceutical product that consists essentially of lyophilized ifosfamide and solutions thereof. The lyophilized ifosfamide of the present invention is suitable for pharmaceutical use, and can be stored in one or more aseptically sealed containers. The present invention further provides a method of producing lyophilized ifosfamide, which method includes freezing a sterile solution of ifosfamide and subjecting it to a primary drying stage. The primary drying stage includes applying a vacuum to remove solvent while raising the temperature to a primary drying temperature, to produce a first intermediate. The first intermediate is subjected to a secondary drying stage, which includes applying a vacuum to further remove solvent while raising the temperature to a secondary drying temperature, to produce the pharmaceutical product. The method of the present invention can be applied toward the production of stable, sterile, essentially pure dosage forms of ifosfamide (e.g., a sterile single-dose ifosfamide product) with doses that are within about 5% of the label claim. The lyophilized ifosfamide of the present invention can be administered to a patient using standard therapeutic methods for delivering ifosfamide.

39 Claims, No Drawings

STERILE LYOPHILIZED IFOSFAMIDE AND ASSOCIATED METHODS

TECHNICAL FIELD OF THE INVENTION

The invention pertains to lyophilized ifosfamide, solutions thereof, and methods of preparing and using lyophilized ifosfamide.

BACKGROUND OF THE INVENTION

Ifosfamide is a chemotherapeutic agent of the formula:

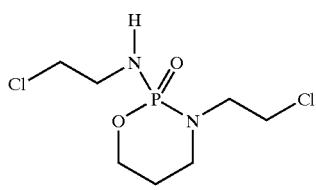

and is described in U.S. Pat. No. 3,732,340. Ifosfamide is sometimes referred to as N,3-bis(2-chloroethyl) tetrahydro-2H-1,3,2-oxazaphosphorin-2-amine-2-oxide, and 3-(2-chloroethyl)-2-[(2-chloroethyl)amino]tetrahydro-2H-1,3,2-oxazaphosphorin-2-oxide. Ifosfamide has the molecular formula $C_7H_{15}Cl_2N_2O_2P$, and has a molecular weight of 261.1. Ifosfamide is manufactured as a white crystalline powder, which has a melting point of about 48–51° C. and which is highly hygroscopic. Ifosfamide begins to sinter at temperatures below its melting point and, therefore, must be stored at relatively low temperatures (room temperature or below). In addition, contact with moisture in the air should be avoided whenever possible. Ifosfamide dissolves in water to the extent of at least about 10 wt %, but has limited stability in an aqueous solution (reported in some references as about 3–4 hours at 20–22° C., or 36 hours at 4–6° C.).

Ifosfamide is approved in the U.S. for third-line chemotherapy of germ cell testicular cancer and is ordinarily used in combination with a prophylactic agent for hemorrhagic cystitis, such as mesna. Ifosfamide is presently marketed in the U.S. under the name IFEX®, which is supplied as a crystalline powder and is stored in 1 g and 3 g single dose vials. For therapeutic applications, the powder is dissolved in a sterile aqueous vehicle such as Sterile Water for Injection, USP; or a sterile aqueous vehicle that contains a bacteriostat, e.g., Sterile Bacteriostatic Water for Injection, USP (preserved with benzyl alcohol or parabens), and is administered by injection. Typically, the 1 g and 3 g dosage forms are constituted in 20 mL and 60 mL of the aqueous vehicle, respectively, to achieve a final concentration of 50 mg/mL. Solutions of ifosfamide may be diluted further to achieve concentrations of 0.6–20 mg/mL in injectable fluids such as 5% Dextrose Injection, USP; 0.9% Sodium Chloride Injection, USP; Lactated Ringer's Injection, USP; or Sterile Water for Injection, USP.

Ifosfamide is normally administered intravenously at a dosage of about 1.2 $g/m^2$ per day for five consecutive days. Treatment is repeated every 3 weeks or after recovery from hematologic toxicity. The duration of the infusion is generally about 30 minutes, but may be 1 to 2 hours. Ifosfamide solutions should be refrigerated and be used within 24 hours. See, e.g., *Physicians' Desk Reference*, 56th Ed., Medical Economics Co., Inc., Montvale, N.J., pp. 1123–1124 (2002).

The manufacture of ifosfamide sterile powder involves a powder fill operation that presents a number of practical problems. During the production of the sterile powder, the powder is processed in a way that causes variations in the flow properties. The variation in flow properties greatly impairs the accuracy of dosage during the filling process. The sterile powder fill operation further employs specialized equipment. The powder fill operation is costly and may be further complicated by the risk of microbial contamination during the operation. Moreover, the powder fill process creates risks of accidental exposure to the powder by personnel that are involved in the production process. The processing and storage of ifosfamide powder is still further complicated by its hygroscopic properties, sensitivity to heat, and relatively low melting point. If the powder is stored for a long period of time, the product sinters and its dissolution time increases significantly.

Various approaches for manufacturing lyophilized forms of ifosfamide have been proposed. For example, U.S. Pat. Nos. 5,750,131 and 5,972,912 describe the lyophilization of one or more amino acids in combination with ifosfamide. U.S. Pat. No. 5,204,335 describes the lyophilization of hexitols in combination with ifosfamide, and U.S. Pat. No. 4,959,215 describes the lyophilization of hexitols in combination with ifosfamide/mesna mixtures. In addition, U.S. Pat. No. 5,227,373 describes the lyophilization of urea in combination with ifosfamide.

While the lyophilization processes described above overcome some of the problems associated with the crystalline powder, such processes are disadvantageous in that they utilize auxiliary materials such as amino acids, hexitols and urea, are not present in the product that is approved for human chemotherapy. Thus, there remains a need for a stable, sterile form of lyophilized ifosfamide that contains no auxiliary materials, and methods of producing such a product. The invention provides such a product and production processes. These and other advantages of the present invention, as well as additional inventive features, will be apparent from the description of the invention provided herein.

BRIEF SUMMARY OF THE INVENTION

The present invention provides a stable, sterile, pharmaceutical product that consists essentially of lyophilized ifosfamide. The lyophilized ifosfamide of the present invention is preferably contained in within a container that is aseptically sealed. Preferably, the container contains a therapeutically effective amount of the ifosfamide of the present invention and is of sufficient volume to contain the volume of solution that is recommended for constitution. The present invention further provides a solution prepared by dissolving the lyophilized ifosfamide of the present invention in an aqueous vehicle, such as a sterile aqueous solvent that is suitable for injection.

The present invention further provides a method of producing lyophilized ifosfamide, which method includes freezing a sterile aqueous solution of ifosfamide to produce a frozen mixture;

subjecting the frozen mixture to a primary drying stage, which includes applying a vacuum to reduce the pressure by an amount or to a level that is effective to remove the aqueous solvent from the frozen mixture, and, while applying the vacuum, raising the temperature to a primary drying temperature, to produce a first intermediate; and subjecting the first intermediate to a secondary drying stage, which includes applying a vacuum to reduce the pressure by an amount or to a level that is effective to remove the aqueous solvent from the first intermediate, and, while applying the vacuum, raising the temperature to a secondary drying temperature, to produce the pharmaceutical product.

The method of the present invention can be applied toward the production of stable, sterile, essentially pure dosage forms of ifosfamide (e.g., a sterile single-dose ifosfamide product), which method includes:

filling one or more containers, each container defining an opening, with a sterile solution consisting essentially of a therapeutically effective amount of ifosfamide and an aqueous solvent;

subjecting the sterile solution in the one or more containers to the present method of producing lyophilized ifosfamide; and sealing the opening of the one or more containers, to produce the pharmaceutical product.

The dosage form prepared in accordance with the present invention preferably contains a dosage that is within about 5% of the label claim. The lyophilized ifosfamide of the present invention can be administered to a patient using standard therapeutic methods for delivering ifosfamide (e.g., by injection).

DETAILED DESCRIPTION OF THE INVENTION

The present invention provides a stable, sterile, pharmaceutical product that consists essentially of lyophilized ifosfamide. The lyophilized ifosfanlide of the present invention is a white to off-white solid of high purity and has a low moisture content. The lyophilized ifosfamide of the present invention is preferably greater than 98% pure (i.e., contains less than 2% total impurities based on the total weight of ifosfamide), and is more preferably greater than 99% pure (i.e., contains less than about 1% impurities). Preferably, the lyophilized ifosfamide of the present invention has a moisture content of less than about 1 wt % (% water based on the weight of ifosfamide). More preferably the moisture content is about 0.8 wt % or less, and still more preferably is about 0.5 wt % or less. Most preferably, the lyophilized ifosfamide of the present invention has a moisture content of about 0.3 wt % or less.

The lyophilized ifosfamide of the present invention can be contained within a sealed container. Preferably, the lyophilized ifosfamide of the present invention is contained within a container that is sealed aseptically. More preferably, the container is provided with an opening and a means for aseptically sealing the opening, e.g., such that the sealed container is fluidly sealed or the sealed opening is substantially impermeable to atmospheric gasses, moisture, pathogenic microorganisms, or the like. The container can be constructed of any suitable material such as, for example, glass, polypropylene, Daikyo Resin CZ (sold by Daikyo Gomu Seiko, Ltd.), polyethylene terephthalate, and the like. In a preferred embodiment, the container is constructed of glass. Suitable glass containers include, but are not limited to, glass vials. Suitable glass vials include molded glass vials such as, for example, Type I molded glass vials, and the like. Such molded glass vials can be obtained from Kimble Glass, Inc., Vineland, N.J.; Wheaton Science Products, Miliville, N.J., or other companies.

A suitable means for sealing the container can include, for example, a stopper, a cap, a lid, a closure, a covering which fluidly seals the container, or the like. Examples of suitable closures include closures that are suitable for medical vials, such as those described in U.S. Pat. No. 4,671,331 and references cited therein. The means for sealing the container are not limited to separate closures or closure devices, but also includes self-sealing containers and containers which are manufactured and sealed during filling operations. In a preferred embodiment, the means for aseptically sealing the container includes a stopper such as, for example, a stopper that is configured to fluidly seal the opening. Suitable stoppers include conventional medical grade stoppers which do not degrade or release significant amounts of impurities upon exposure to the constituted aqueous ifosfamide solution. Preferably, the stopper is constructed of an elastomer, which is more preferably an elastomer that is pierceable by a hypodermic needle or a blunt cannula. Exemplary stoppers include 6720 GC gray rubber stoppers from American Stelmi Corporation, 4432/50 gray rubber stoppers from West Company, and the like.

Optionally, an outer seal is provided which covers and entirely surrounds the stopper. The outer seal can be constructed of any suitable material. When an outer seal is used, it is preferably fitted with a lid that can be easily manually removed to provide access to the stopper. Suitable outer seals can include, for example, Flip-off Aluminum/Polypropylene Seals (lacquered or non-lacquered aluminum), marketed by The West Company, Inc., and other manufacturers. Such seals include an outer rim made of a suitable material, such as aluminum, that entirely surrounds the lateral edge of the stopper and further include a lid (typically polypropylene or other suitable material) that entirely covers the upper surface of the stopper. The polypropylene lid can be "flipped" off e.g., by exerting upward pressure with a finger or thumb, to provide access to the stopper which, in turn, provides access to the stopper, e.g., so that it can be punctured with a hypodermic needle to deliver an aqueous vehicle for constitution. See, e.g., U.S. Pat. No. 6,136,814.

Preferably, the container contains a therapeutically effective dose of the ifosfamide of the present invention and is of sufficient volume to contain the volume of solution that is recommended for constitution. More preferably, the container contains ifosfamide in an amount which is an approved dosage for human chemotherapy and is of sufficient volume to contain the total volume of solution recommended for constitution. In a particularly preferred embodiment, the container volume is about 30 mL, and about 1.0 g of the lyophilized ifosfamide of the present invention are contained within the container. In another particularly preferred embodiment, the container volume is about 100 mL, and about 3.0 g of lyophilized ifosfamide of the present invention are contained within the container.

The present invention includes solutions prepared by dissolving the lyophilized ifosfamide manufactured in accordance with the method of the present invention dissolved in an aqueous vehicle. The aqueous vehicle is preferably a sterile aqueous vehicle that is normally used as liquid vehicle for injection. Suitable aqueous vehicles include, for example, sterile water (e.g., Sterile Water for Injection, USP) and sterile aqueous vehicles that contain a bacterial growth inhibiting-effective amount of one or more bacteriostatic agents, e.g., Sterile Bacteriostatic Water for Injection, USP (preserved with benzyl alcohol or parabens), as described herein, and the like.

The present invention further provides a method of producing the lyophilized ifosfamide of the present invention, which method includes freezing a sterile aqueous solution, to produce a frozen mixture;

subjecting the frozen mixture to a primary drying stage, which includes applying a vacuum to reduce the pressure by an amount or to a level that is effective to remove aqueous solvent from the frozen mixture, and, while applying the vacuum, raising the temperature to a primary drying temperature, to produce a first intermediate; and subjecting the first intermediate to a secondary drying stage, which includes applying a vacuum to reduce the pressure by an amount that is effective to remove aqueous solvent from the first intermediate, and, while applying the vacuum, raising the temperature to a secondary drying temperature, to produce the pharmaceutical product.

The sterile solution preferably consists essentially of ifosfamide and an aqueous solvent. The sterile solution can have an ifosfamide concentration up to about 130 mg/mL or even greater, but more typically has a concentration of about 130 mg/mL or less (e.g., from about 10 mg/mL to about 130 mg/mL). Preferably, the sterile solution has a concentration of about 100 mg/mL or less (e.g., from about 10–100 mg/mL), but more preferably has a concentration of from about 30–100 mg/mL, and still more preferably has a concentration of from about 50–100 mg/mL. In a particularly preferred embodiment, the sterile solution has a concentration of about 100 mg/mL.

The sterile solution is "frozen" or cooled to a temperature that freezes the aqueous solvent. Preferably, the sterile solution is frozen sufficiently to allow for its removal under reduced pressure (e.g., by sublimation). Preferably, the sterile solution is frozen to a temperature of about −10° C. or lower (e.g., from about −10° C. to about −70° C., from about −20° C. to about −70° C., from about −30° C. to about −70° C., or from about −30° C., to about −60° C.), but is more preferably frozen to a temperature of about −40° C. or lower (e.g., from about −40° C. to about −60° C.). Most preferably, the sterile solution is frozen to a temperature of about −50° C. or lower (e.g., from about −50° C. to about −60° C.).

The sterile solution can be frozen rapidly (e.g., by contacting a container of the solution in a cooling bath), or by cooling in stages (e.g., by lowering the temperature incrementally at progressively lower temperatures until the frozen mixture is obtained). Alternatively, the sterile solution can be frozen by continuously cooling at a substantially constant rate until the frozen mixture is obtained. For example, the sterile solution can be frozen by cooling at a substantially constant rate of about 5° C. per minute or less (e.g., from about 0.1–5° C. per minute), at a rate of about 3° C. per minute or less (e.g., from about 0.1–3° C. per minute), at a rate of about 2° C. per minute or less (e.g., from about 0.1–2° C. per minute), or at a rate of about 1° C. per minute or less (e.g., from about 0.1–1° C. per minute, or from about 0.1–0.5° C. per minute), until the frozen mixture is obtained. Alternatively, the sterile solution can be frozen using a combination of incremental cooling stages and one or more continuous cooling cycles (e.g., continuously cooling at a substantially constant rate) until the frozen mixture is obtained.

The primary drying temperature is preferably from about −40° C. to about 25° C., but is more preferably from about −30° C. to about 15° C., and is even more preferably from about −20° C. to about 10° C., and is still more preferably from about −15° C. to about 0° C. Most preferably, the primary drying temperature is from about −15° C. to about −5° C. (e.g., about −10° C.). In the primary drying stage, the temperature can be raised in stages (e.g., raised incrementally at progressively higher temperatures until the primary drying temperature is attained). Alternatively, the temperature of the primary drying stage can be raised continuously (e.g., at a substantially constant rate) until the primary drying temperature is attained. Preferably, the temperature of the primary drying stage is raised at a rate of about 5° C. per minute or less (e.g., from about 0.1–5° C. per minute). More preferably, the temperature of the primary drying stage is raised at a rate of about 3° C. per minute or less (e.g., from about 0.1–3° C. per minute). Still more preferably, the temperature of the primary drying stage is raised at a rate of about 2° C. per minute or less (e.g., from about 0.1–2° C. per minute). Most preferably, the temperature of the primary drying stage is raised at a rate of about 1° C. per minute or less (e.g., from about 0.1–1° C. per minute, or from about 0.1–0.5° C. per minute). In a particularly preferred embodiment, the temperature in the primary drying stage is raised at a rate of about 0.5° C. per minute or less (e.g., about 0.5° C. per minute, or about 0.2° C. per minute).

The primary drying temperature in the primary drying stage is preferably maintained (e.g., held at a substantially constant temperature or kept within a particular range) until substantially all of the aqueous solvent is removed. The removal of substantially all of the aqueous solvent can be determined by visual inspection. Alternatively, the removal of substantially all of the aqueous solvent can be determined on the basis of when the increase in the temperature of the frozen mixture (internal temperature) becomes insignificant. Normally, as the temperature is raised during the primary drying stage, the internal temperature "lags" behind (i.e., is lower than) the external temperature (sometimes referred to as the "shelf temperature"). In some instances when the external temperature is raised during the primary drying stage, the internal temperature can lag behind the external temperature by as much as about 10° C., or even more. Typically, the removal of substantially all of the solvent can be determined by comparing the internal temperature with the external temperature. The temperature of the frozen mixture and the external temperature can be measured using any suitable means, e.g., a thermometer, a thermocouple, or the like. In most instances, substantially all of the aqueous solvent is removed when the internal temperature remains steady or is about equal to (e.g., is slightly less than, is equal to, or slightly exceeds) the external temperature. In a preferred embodiment, the primary drying temperature is maintained until the temperature of the frozen mixture is about equal to the primary drying temperature.

The secondary drying temperature in the secondary drying stage can range from about 0° C. to about 40° C., but is preferably from about 10° C. to about 40° C. More preferably, the secondary drying temperature is about ambient temperature (e.g., from about 15° C. to about 30° C.), which is still more preferably from about 20–30° C., and is most preferably from about 20–25° C. (e.g., about 25° C.). In the secondary drying stage, the temperature can be raised at a rate which is the same or different than the rate at which the temperature is raised in the primary drying stage. For example, the temperature in the secondary drying stage can be raised in stages (e.g., raised incrementally at progressively higher temperatures until the secondary drying temperature is attained). Alternatively, the temperature in the secondary drying stage can be raised continuously (e.g., at a substantially constant rate) until the secondary drying temperature is attained. Preferably, the temperature of the secondary drying stage is raised at a rate of about 5° C. per minute or less (e.g., from about 0.1–5° C. per minute). More preferably, the temperature of the secondary drying stage is raised at a rate of about 3° C. per minute or less (e.g., from about 0.1–3° C. per minute). Still more preferably, the temperature of the secondary drying stage is raised at a rate of about 2° C. per minute or less (e.g., from about 0.1–2° C. per minute). Most preferably, the temperature of the primary drying stage is raised at a rate of about 1° C. per minute or less (e.g., from about 0.1–1° C. per minute, or from about 0.1–0.5° C. per minute). In a particularly preferred embodiment, the temperature in the primary drying stage is raised at a rate of about 0.50° C. per minute or less (e.g., about 0.5° C. per minute, or about 0.20° C. per minute).

Preferably, the secondary drying temperature in the secondary drying stage is maintained until the moisture content is less than about 1 wt % relative to the ifosfamide. More preferably, the secondary drying temperature in the secondary drying stage is held until the moisture content is about 0.5 wt % or less relative to the ifosfamide. Most preferably, the secondary drying temperature in the secondary drying stage is held until the moisture content is about 0.3 wt % or less relative to the ifosfamide.

The primary drying stage is preferably carried out at a pressure of about 1 Torr (1000 mTorr, 133 Pa) or less, e.g., from about 10–1000 mTorr (1.33–133 Pa), but is more preferably carried out at a pressure of about 500 mTorr (66.7 Pa) or less, e.g., from about 10–500 mTorr (1.33–66.7 Pa). Still more preferably, the primary drying stage is carried out at a pressure of about 200 mTorr (26.7 Pa) or less, e.g., from about 10–200 mTorr (1.33–26.7 Pa). Most preferably, the primary drying stage is carried out at a pressure of about 150 mTorr (20 Pa) or less, e.g., from about 10–150 mTorr (1.33–20 Pa). In a particularly preferred embodiment, the primary drying stage is carried out at a pressure of about 100 mTorr (13.3 Pa) or less, e.g., from about 10–100 mTorr (1.33–13.3 Pa).

The secondary drying stage can be carried out at a pressure which is the same or different than the pressure at which the primary drying stage is carried out. Preferably, the secondary drying stage is carried out at a pressure of about 1 Torr (1000 mTorr, 133 Pa) or less, e.g., from about 10–1000 mTorr (1.33–133 Pa), but is more preferably carried out at a pressure of about 500 mTorr (66.7 Pa) or less, e.g., from about 10–500 mTorr (1.33–66.7 Pa), and is still more preferably carried out at a pressure of about 200 mTorr (26.7 Pa) or less, e.g., from about 10–200 mTorr (1.33–26.7 Pa). Most preferably, the secondary drying stage is carried out at a pressure of about 150 mTorr (20 Pa) or less, e.g., from about 10–150 mTorr (1.33–20 Pa). In a particularly preferred embodiment, the secondary drying stage is carried out at a pressure of about 100 mTorr (13.3 Pa) or less, e.g., from about 10–100 mTorr (1.33–13.3 Pa).

The method of the present invention can be applied toward the production of stable, sterile, essentially pure dosage forms of ifosfamide (e.g., sterile single-dose or multiple-dose ifosfamide products). Exemplary pharmaceutical dosage forms include a pharmaceutical dosage form comprising a sealed container (e.g., a container as described herein) and a pharmaceutical product consisting essentially of a therapeutically effective amount of lyophilized ifosfamide contained within the container. The pharmaceutical dosage form of the present invention preferably includes a dose of about 1.0 g or about 3.0 g of the lyophilized ifosfamide contained within the container.

The method of the present invention can consistently and reproducibly produce dosage forms with high dosage accuracy and low variability in the dosage. Moreover, the method of the present invention is simpler and is significantly less costly than the conventional methods used in the production of ifosfamide crystalline powder. In one aspect, the present invention includes a method of producing a stable, sterile pharmaceutical product consisting essentially of lyophilized ifosfamide, which includes:

filling one or more containers with a sterile solution consisting essentially of a therapeutically effective amount of ifosfamide and an aqueous solvent, each container defining an opening;

subjecting the sterile solution in the one or more containers to the lyophilized ifosfamide production method described herein; and sealing the opening of the one or more containers, to produce the pharmaceutical product.

The method of the present invention preferably includes:

aseptically filling one or more containers, each container defining an opening, with a sterile solution consisting essentially of a therapeutically effective amount of ifosfamide and an aqueous solvent;

freezing the sterile solution in the one or more containers, to produce a frozen mixture;

subjecting the frozen mixture to a primary drying stage, which includes applying a vacuum to reduce the pressure by an amount effective to remove aqueous solvent from the frozen mixture, and, while applying the vacuum, raising the temperature to a primary drying temperature, to produce a first intermediate; and subjecting the first intermediate to a secondary drying stage, which comprises applying a vacuum to reduce the pressure by an amount effective to remove aqueous solvent from the first intermediate, and, while applying the vacuum, raising the temperature to a secondary drying temperature, to produce a sterile solid consisting essentially of ifosfamide in the one or more containers; and aseptically sealing the opening(s) of the one or more containers, to produce the pharmaceutical product, wherein the frozen mixture, the primary and secondary drying stages, and the one or more containers are as described herein.

The one or more containers preferably include one or more sterile vials, preferably glass vials, as described herein. The sealing step preferably includes sealing the opening using the means for aseptically sealing the opening described herein. The sealing means preferably includes a stopper as described herein. The sterile solution preferably has an ifosfamide concentration of about 130 mg/mL or less, more preferably about 100 mg/mL or less. In a particularly preferred embodiment, the concentration of the sterile solution is about 100 mg/mL and the one or more containers (which are most preferably vials) are filled with 10.0 mL or 30.0 mL of the sterile solution, to provide a final dosage of 1.0 g or 3.0 g of ifosfamide, respectively.

The dosage form prepared in accordance with the present invention preferably is within about 5% of the label claim. In other words, the amount of ifosfamide in the container (as determined by a suitable analytical technique, e.g., HPLC, ifosfamide assay, or the like) preferably is within about 5 wt % of the ifosfamide dosage claimed in product label. By way of example, for 1 g dosage vials prepared in accordance with the present invention, with a label claim of 1.0 g of ifosfamide, the amount of ifosfamide in the vials, as determined by a suitable analytical technique, preferably is within about 0.95–1.05 g. For 3.0 g dosage vials prepared in accordance with the present invention, with a label claim of 3.0 g of ifosfamide, the amount of ifosfamide in the vials, as determined by a suitable analytical technique, preferably is within about 2.85–3.15 g. More preferably, the product prepared in accordance with the present invention has an actual dosage that is within about 4% of the label claim. Most preferably, the product prepared in accordance with the present invention has an actual dosage that is within about 3% of the label claim.

The lyophilized ifosfamide of the present invention can be administered to a patient in need thereof (e.g., for chemotherapy) using standard therapeutic methods for delivering ifosfamide including, but not limited to, the methods described herein. The lyophilized ifosfamide of the present invention is preferably administered by dissolving a therapeutically effective amount of the lyophilized ifosfamide of the present invention in a pharmaceutically acceptable solvent to produce a pharmaceutically acceptable solution, and administering the solution (preferably by injection) to the patient.

The lyophilized ifosfamide of the present invention may be constituted for parenteral administration to a patient using any pharmaceutically acceptable diluent. Preferably, the diluent is Sterile Water for Injection, USP. Alternatively, Sterile Bacteriostatic Water for Injection, USP (benzyl alcohol or parabens preserved) may be used as a diluent. Any quantity of diluent may be used to constitute the lyophilized ifosfamide such that a suitable solution for injection is prepared. Accordingly, the quantity of diluent must be sufficient to dissolve the lyophilized ifosfamide. Typically, 20–60 mL of diluent are used to constitute the lyophilized ifosfamide to yield a final concentration of about 50 mg/mL. Constituted solutions of lyophilized ifosfamide should be administered to a patient promptly upon constitution. Alternatively, constituted solutions may be refrigerated and used within 24 hours.

Solutions of ifosfamide may be further diluted after constitution to achieve concentrations of about 0.6 to about 20 mg/mL. Suitable fluids for further dilution of solutions of constituted lyophilized ifosfamide include, by way of example, 5% Dextrose Injection USP, 0.9% Sodium Chloride Injection USP, Lactated Ringer's Injection USP, and Sterile Water for Injection USP.

The following examples further illustrate the present invention but, of course, should not be construed as in any way limiting its scope.

EXAMPLE 1

This example demonstrates a procedure for preparing a sterile aqueous ifosfamide solution.

A quantity of sterile water for injection ("WFI") was collected (approximately 85% of total batch quantity) and was placed into a clean, jacketed Type 316 stainless steel compounding tank. The WFI was at a temperature of about 15–25° C., and nitrogen gas was bubbled through. Ifosfamide, USP raw material (obtained from a commercial supplier, 26.40 kg) was added to the WFI in the compounding tank. The resulting mixture was stirred at 400–700 rpm until the ifosfamide was completely dissolved in the WFI (at least 15 minutes).

After the ifosfamide was dissolved, the batch volume was raised to 264.0 L (total batch quantity) by the addition of WFI, USP, and the solution was stirred at 400–700 rpm for an additional 10 minutes. The solution was then cooled to a temperature between 2° C. and 8° C. with continuous stirring at 400–700 rpm.

Prior to filtration, an in-process sample was taken from the batch tank, and was subjected to an appearance test (visual examination) and ifosfamide assay were carried out. After completion of the in-process appearance test and ifosfamide assay, the cooled solution of ifosfamide in WFI was pumped through a 0.22 μm pre-filter (Millipak® PVDF available from Millipore Corporation) into a filling room using Tygon® tubing. The ifosfamide solution was continuously stirred at 400–700 rpm and bubbled with $N_2$ during the entire filtration process. The pre-filter was rinsed with WFI, USP prior to filtration of the ifosfamide solution. Near the end of the filtration step, a sample was collected and subjected to a pre-filtration bioburden test to determine the action limit of the material, which should be not more than 10 CFU/mL.

Following pre-filtration, the ifosfamide solution was passed through a sterile 0.22 μm final filter (Millipak® PVDF available from Millipore Corporation) and the filtrate was delivered into a clean, sterile receiving carboy using silicone tubing. In a class 100 clean room environment, sterile vials were aseptically filled with the solution and partially stoppered.

EXAMPLE 2

This example demonstrates a method of lyophilizing ifosfamide.

A nitrogen supply was connected to a sterilizing filter assembly on a lyophilizer and the lyophilizer chamber and condenser were steam sterilized for at least 30 minutes using standard sterilization procedures. The minimum chamber drain temperature and minimum condenser drain temperature were each at least 121.0° C. After sterilization, a vessel integrity test was performed. The shelves and condenser plates of the lyophilizer were chilled to –30° C. and –50° C., respectively, and the vessel was leak tested.

The lyophilization process was initiated by pre-chilling the shelves of the lyophilizer. The shelf temperature controller was adjusted to a set point of 50 C. After the pre-chill set point was reached, the shelves were loaded with vials containing an ifosfamide solution prepared as described in Example 1 over approximately 5 hours. After the product solution was completely loaded, the chamber door was closed and the shelf temperature was maintained at the pre-chill set point for at least 60 minutes. The shelf temperature controller was then adjusted to a set point of –35° C. with a ramp time of 80 minutes and the shelf temperature was held at the set point temperature of –35° C. for at least 10 minutes. The shelf temperature controller was then adjusted to a set point of –50° C. with a ramp time of 150 minutes and the shelf temperature was held at the set point temperature of –50° C. for at least 16 hours. The condenser was then chilled to below –50° C.

When the condenser temperature reached –50° C., the primary drying step was performed. The vacuum controller set point was set to 100 mTorr (13.3 Pa) and the vacuum alarm high set point was set to 150 mTorr (20.0 Pa). Nitrogen gas was used to regulate the pressure. The shelf temperature controller was adjusted to a primary drying set point of –10° C. with a ramp time of 80 minutes and the shelf temperature was held at the drying set point temperature of –10° C. for 134.5 hours.

The shelf temperature controller was adjusted to a secondary drying set point of +26° C. with a ramp time of 180 minutes and the shelf temperature was held at the secondary drying set point temperature of 26° C. for at least 48 hours. At the end of the 48 hour secondary drying hold time, the chamber was isolated and the vacuum was released. The pressure was raised to atmospheric pressure by addition of sterile nitrogen gas. The samples were submitted to an in-process moisture check to determine the amount of moisture remaining in the vials. After confirming that the samples contained a sufficiently low moisture level (i.e., not more than 0.3%), the chamber was isolated and sterile nitrogen gas was added until a pressure of about 12 PSIA was reached.

The vials containing the lyophilized product were then stoppered with Stelmi 6720GC Gray Lyo stoppers using an internal stoppering mechanism. At the completion of the stoppering step, the chamber was again isolated and the vacuum released. The pressure was raised to atmospheric pressure by addition of sterile nitrogen gas. The lyophilizer chamber was unloaded and the stoppered vials containing lyophilized product were conveyed to a capping machine and sealed with aluminum seals. The vials were then inspected, labeled, and packaged.

The final product was a sterile, white to off-white solid having greater than 99% purity and was suitable for administration by injection. The moisture content of the final product was not more than 0.3%. Solutions prepared by dissolving the final product in Sterile Water for Injection were clear and free of particulates.

EXAMPLE 3

This example demonstrates a procedure for preparing a sterile aqueous ifosfamide solution.

A quantity of sterile water for injection ("WFI") was collected (approximately 85% of total batch quantity) and was placed into a clean, jacketed Type 316 stainless steel compounding tank. The WFI was at a temperature of about 15–25° C., and nitrogen gas was bubbled through. Ifosfamide, USP raw material (obtained from a commercial supplier, 52.50 kg) was added to the WFI in the compounding tank. The resulting mixture was stirred at 400–700 rpm until the ifosfamide was completely dissolved in the WFI (at least 15 minutes).

After the ifosfamide was dissolved, the batch volume was raised to 525.0 L (total batch quantity) by the addition of WFI, USP, and the solution was stirred at 400–700 rpm for an additional 10 minutes. The solution was then cooled to a temperature between 2° C. and 8° C. with continuous stirring at 400–700 rpm.

Prior to filtration, an in-process sample was taken from the batch tank and was subjected to an appearance test (visual examination) and ifosfamide assay were carried out. After completion of the in-process appearance test and ifosfamide assay, the cooled solution of ifosfamide in WFI was pumped through a 0.22 μm pre-filter (Millipak® PVDF available from Millipore Corporation) into a filling room using Tygon® tubing. The ifosfamide solution was continuously stirred at 400–700 rpm and bubbled with $N_2$ during the entire filtration process. The pre-filter was rinsed with WFI, USP prior to filtration of the ifosfamide solution. Near the end of the filtration step; a sample was collected and subjected to a pre-filtration bioburden test to determine the action limit of the material, which should be not more than 10 CFU/mL.

Following pre-filtration, the ifosfamide solution was passed through a sterile 0.22 μm final filter (Millipak® PVDF available from Millipore Corporation) and the filtrate was delivered into a clean, sterile receiving carboy using silicone tubing. In a class 100 clean room environment, sterile vials were aseptically filled with the solution and partially stoppered.

EXAMPLE 4

This example demonstrates a method of lyophilizing ifosfamide.

An ifosfamide solution prepared as described in Example 3 was lyophilized using the lyophilization procedure described in Example 2. The properties of the final product were consistent with the properties of the final product obtained in Example 2.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A stable, sterile pharmaceutical product consisting essentially of lyophilized ifosfamide.

2. The product of claim 1, wherein the lyophilized ifosfamide comprises less than about 0.5 wt % water.

3. The product of claim 1, wherein the lyophilized ifosfamide is in the form of a white to off-white solid.

4. The product of claim 1, contained within a sealed container.

5. The product of claim 4, wherein the container has a volume of about 30 mL, and about 1.0 g of lyophilized ifosfamide are contained within the container.

6. The product of claim 4, wherein the container has a volume of about 100 mL, and about 3.0 g of lyophilized ifosfamide are contained within the container.

7. The product of claim 4, wherein the container defines an opening and comprises a means for sealing the opening.

8. The product of claim 7, wherein the container is a glass vial.

9. The product of claim 7, wherein the means for sealing the opening comprises a stopper.

10. The product of claim 9, wherein the stopper is pierceable by a hypodermic needle or a blunt cannula.

11. The product of claim 9, further comprising an outer seal which covers and entirely surrounds the stopper.

12. The product of claim 9, wherein the outer seal comprises a lid which is manually removable, to provide access to the stopper.

13. The product of claim 12, wherein the outer seal comprises an outer rim and a polypropylene lid, wherein the aluminum rim surrounds the lateral edge of the stopper and the polypropylene lid entirely covers the upper surface of the stopper.

14. A solution prepared by dissolving the product of claim 1 in an aqueous vehicle.

15. A method of producing a stable, sterile pharmaceutical product consisting essentially of lyophilized ifosfarnide, the method comprising:
 freezing a sterile solution consisting essentially of ifosfamide and an aqueous solvent to a temperature of from about −10° C. to about −70° C., to produce a frozen mixture;
 subjecting the frozen mixture to a primary drying stage, which comprises applying a vacuum to reduce the pressure by an amount effective to remove aqueous solvent from the frozen mixture, and, while applying the vacuum, raising the temperature to a primary drying temperature, wherein the primary drying temperature is from about −40° C. to about 25° C., to produce a first intermediate; and
 subjecting the first intermediate to a secondary drying stage, which comprises applying a vacuum to reduce the pressure by an amount effective to remove aqueous solvent from the first intermediate, and, while applying the vacuum, raising the temperature to a secondary drying temperature, wherein the secondary drying temperature is from about 0° C. to about 40° C., to produce the pharmaceutical product.

16. The method of claim 15, wherein the primary drying stage is carried out at a pressure of about 1000 mTorr or less.

17. The method of claim 16, wherein the primary drying stage is carried out at a pressure of about 200 mTorr or less.

18. The method of claim 15, wherein the sterile solution is frozen to a temperature of from about −30° C. to about −70° C.

19. The method of claim 18, wherein the sterile solution is frozen to a temperature of from about −40° C. to about −60° C.

20. The method of claim 15, wherein the primary drying temperature is from about −20° C. to about 10° C.

21. The method of claim 20, wherein the primary drying temperature is from about −15° C. to about −5° C.

22. The method of claim 15, wherein the temperature in the primary drying stage is raised at a rate of about 5° C. per minute or less.

23. The method of claim 22, wherein the temperature in the primary drying stage is raised at a rate of from about 0.1–3° C. per minute.

24. The method of claim 15, wherein the primary drying temperature in the primary drying stage is maintained until substantially all of the aqueous solvent is removed.

25. The method of claim 15, wherein the primary drying temperature in the primary drying stage is maintained until the temperature of the frozen mixture is about equal to the primary drying temperature.

26. The method of claim 15, wherein the secondary drying stage is carried out at a pressure of about 1000 mTorr or less.

27. The method of claim 26, wherein the secondary drying stage is carried out at a pressure of about 200 mTorr or less.

28. The method of claim 15, wherein the secondary drying temperature is from about 10° C. to about 40° C.

29. The method of claim 28, wherein the secondary drying temperature is from about 20° C. to about 30° C.

30. The method of claim 15, wherein the temperature in the secondary drying stage is raised at a rate of about 5° C. per minute or less.

31. The method of claim 30, wherein the temperature in the secondary drying stage is raised at a rate of from about 0.1–3° C. per minute.

32. The method of claim 15, wherein the secondary drying temperature in the secondary drying stage is held until the moisture content is about 0.5 wt % or less relative to the ifosfamide.

33. A method of administering ifosfamide to a patient in need thereof, the method comprising:
 dissolving the pharmaceutical product of claim 1 in a pharmaceutically acceptable solvent to produce a pharmaceutically acceptable solution; and
 administering the solution to the patient.

34. A method of producing a stable, sterile pharmaceutical product consisting essentially of lyophilized ifosfamide, the method comprising:
 filling one or more containers, each container defining an opening, with a sterile solution consisting essentially of a therapeutically effective amount of ifosfamide and an aqueous solvent;
 freezing the sterile solution in the one or more containers to a temperature of from about −30° C. to about −70° C., to produce a frozen mixture;
 subjecting the frozen mixture to a primary drying stage, which comprises applying a vacuum to reduce the pressure by an amount effective to remove aqueous solvent from the frozen mixture, and, while applying the vacuum, raising the temperature to a primary drying temperature, wherein the primary drying temperature is from about −40° C. to about 25° C., to produce a first intermediate;
 subjecting the first intermediate to a secondary drying stage, which comprises applying a vacuum to reduce the pressure by an amount effective to remove aqueous solvent from the first intermediate, and, while applying the vacuum, raising the temperature to a secondary drying temperature, wherein the secondary drying temperature is from about 0° C. to about 40° C., to produce a solid consisting essentially of ifosfamide in the one or more containers; and
 sealing the opening of the one or more containers, to produce the pharmaceutical product.

35. The method of claim 34, wherein the one or more containers comprises one or more sterile glass vials and the sealing step comprises aseptically sealing the opening of the one or more glass vials with a stopper.

36. The method of claim 35, wherein the sterile solution has an ifosfamide concentration of about 130 mg/mL or less.

37. The method of claim 36, wherein the sterile solution has an ifosfamide concentration of about 100 mg/mL or less.

38. A pharmaceutical dosage form comprising a sealed container and a pharmaceutical product consisting essentially of a therapeutically effective amount of lyophilized ifosfamide contained within the container.

39. The pharmaceutical dosage form of claim 38, wherein the amount of lyophilized ifosfamide contained within the container is about 1.0 g or about 3.0 g.

* * * * *